United States Patent [19]

Wolff et al.

[11] Patent Number: 5,756,144
[45] Date of Patent: May 26, 1998

[54] MEDICAL INSTRUMENT WITH A HYDROPHILIC, LOW-FRICTION COATING AND METHOD OF PREPARATION

[75] Inventors: Per Wolff, Birkerod; Hans-Ole Larsen, Farum; Jøgen Kamstrup-Larsen, Allerød, all of Denmark

[73] Assignee: Meadox Medicals, Inc., Oakland, N.J.

[21] Appl. No.: 955,746

[22] PCT Filed: Jun. 17, 1991

[86] PCT No.: PCT/DK91/00163

§ 371 Date: Apr. 29, 1993

§ 102(e) Date: Apr. 29, 1993

[87] PCT Pub. No.: WO91/19756

PCT Pub. Date: Dec. 26, 1991

[30] Foreign Application Priority Data

Jun. 15, 1990 [DK] Denmark ................. 1467/90

[51] Int. Cl.$^6$ ................................ A61L 29/00
[52] U.S. Cl. .............. 427/2.3; 427/2.1; 427/388.4; 427/409; 427/412.1; 428/515
[58] Field of Search ................. 428/35.7, 35.8, 428/35.9, 413, 423.1, 424.7, 425.1, 424.2, 457, 461, 500, 502, 507, 515, 518, 520, 378, 383; 427/2.1, 2.3, 388.4, 409, 412.1; 604/53, 265, 266, 280

[56] References Cited

U.S. PATENT DOCUMENTS

| 4,642,267 | 2/1987 | Creasy et al. ............... 428/413 |
| 4,876,126 | 10/1989 | Takemura et al. ............ 428/35.7 |
| 5,107,852 | 4/1992 | Davidson et al. ............ 128/772 |
| 5,129,890 | 7/1992 | Bates et al. ............... 604/281 |

FOREIGN PATENT DOCUMENTS

| 0093094 | 11/1983 | European Pat. Off. . |
| 0389632 | 10/1990 | European Pat. Off. . |
| 9005162 | 5/1990 | WIPO . |

Primary Examiner—Stevan A. Resan
Attorney, Agent, or Firm—Hoffmann & Baron, LLP

[57] ABSTRACT

A medical instrument with a hydrophilic, low-friction coating is provided. The guidewire includes a metallic core which includes a first layer of a water-insoluble polymer deposited from an aqueous polymer emulsion, such as an acrylic or polyether block amide latex and a second external layer of a water soluble hydrophilic polymer. The guide wire may also include on the metal core a polymer tube which is heat sealed to the exterior surface of the core. The first and second coatings are then formed on the polymer tube. After the two layers are applied, both layers are cured by heating the coated instrument to a temperature above 100° C.

15 Claims, 1 Drawing Sheet

MEDICAL INSTRUMENT WITH A HYDROPHILIC, LOW-FRICTION COATING AND METHOD OF PREPARATION

BACKGROUND OF THE INVENTION

1. Field of the Invention

The present invention relates to a method of providing a medical instrument for insertion into a body cavity, such as a guide wire and a catheter, with a hydrophilic, low-friction coating, comprising the steps of treating the instrument with a first aqueous coating composition to form a inner layer of a water-insoluble polymer and subsequently treating it with a second aqueous coating composition to form an outer layer of a water-soluble hydrophilic polymer.

By providing medical instruments for insertion into body cavities with a coating of the above mentioned type, the insertion of the instrument is facilitated and the risk of damaging body tissue is reduced.

2. Description of the Prior Art

U.S. Pat. No. 4,642,267 (Creasy et al.) discloses a low-friction coating composition consisting of a blend of a first polymer in the form of thermoplastic polyurethane having no reactive isocyanate groups and a second polymer in the form of a hydrophilic poly (N-vinyl lactam).

Low-friction coatings formed by such a polymer blend suffer from the drawback that they do not adhere sufficiently well to e.g. guide wires to prevent the coating from being scraped off during the bendings which such wires inevitably will be exposed to during use.

GB patent specification No. 1,600,963 discloses a method of providing an article with a hydrophilic coating by forming thereon a layer of polyurethane having reactive isocyanate groups and by reacting polyurethane with polyvinylpyrrolidone to form a coating of a polyvinylpyrrolidone-polyurethane interpolymer.

EP patent publication No. 0,093,094 A1 discloses a method of providing the surface of an article of a polymer with a hydrophilic coating having a low-friction coefficient when wetted. In this known method a solution of a compound containing at least two reactive isocyanate groups per molecule is applied to the polymer article and subsequently a polyethylenoxide solution is applied followed by the removal of the solvent in the latter solution by evaporation and curing of the coating thus formed at an elevated temperature.

DK patent application No. 1709/83 discloses a method of forming on a polymer surface a hydrophilic coating having a low-friction coefficient by applying to the surface a solution containing a compound having at least two unreacted isocyanate groups per molecule and subsequently evaporating the solvent followed by application to the polymer surface thus treated of a solution containing a polyvinylpyrrolidone and evaporation of the solvent. Finally, the coating is cured at elevated temperature.

A common feature of the coatings prepared by the methods described in GB patent specification No. 1,600,963, EP patent publication No. 0,093,094 A1 and DK patent application No. 1709/83 is that they involve the use of polyurethanes with reactive isocyante groups which suffer from the drawback that they can form aromatic carcinogenic amines by reaction with water.

A further drawback of said known methods is that in forming the coatings it is necessary to use organic, including toxic, solvents so as to exclude water to prevent an unintentional reaction with the reactive isocyanate groups.

EP patent publication No. 0,166,998 A2 discloses a method of the type mentioned above wherein the article is initially treated with a solution of a polymer having a reactive functional group in a organic solvent which i.a. serves to dissolve or swell either the material of which the articles is made, or optionally a surface layer on the article.

After evaporation of the solvent by drying the article is treated with a solution containing a water-soluble polymer in the form of a cellulosic polymer, a maleic acid anhydride polymer, a polyarylamide or a nylon. Subsequently, the article thus treated is dried to remove the solvent before dipping it into water with the object of increasing the affinity of the coating to water. Eventually, the article thus treated is subjected to a final drying.

EP-A1-0389632 describes medical instruments such as catheters and guide wires coated with a low-friction coating comprising an inner layer of a polymer deposited from a solution of said polymer in an organic solvent and an outer layer of a hydrophilic polymer deposited from a solution of said polymer.

SUMMARY OF THE INVENTION

The use of organic solvents to form the inner layer of the low-friction coating creates both environmental and health problems, and the object of the invention is to provide a method which allows the inner layer as well as the outer layer to be formed without the use of organic solvents.

Another object is to provide a low-friction coating adhering sufficiently strong to the instrument, and in particular to an instrument of metal, to prevent that the coating is removed therefrom during use. The adherence should e.g. be so strong that the low-friction coating on a guide wire is not scraped off when a catheter is axially displaced relative to the guide wire.

A further object of the invention is to provide a coating free of substances presenting a health risk in case parts of the coating are unintentionally released into the human organism, e.g. directly into the blood stream, during use of the coated instrument.

These and other objects which will appear from the following description are obtained with the method according to the invention, which method is characterized in that an aqueous polymer emulsion is used as the first coating composition and that the two layers are cured simultaneously following the application of the second coating composition by heating to a temperature of above 100° C.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
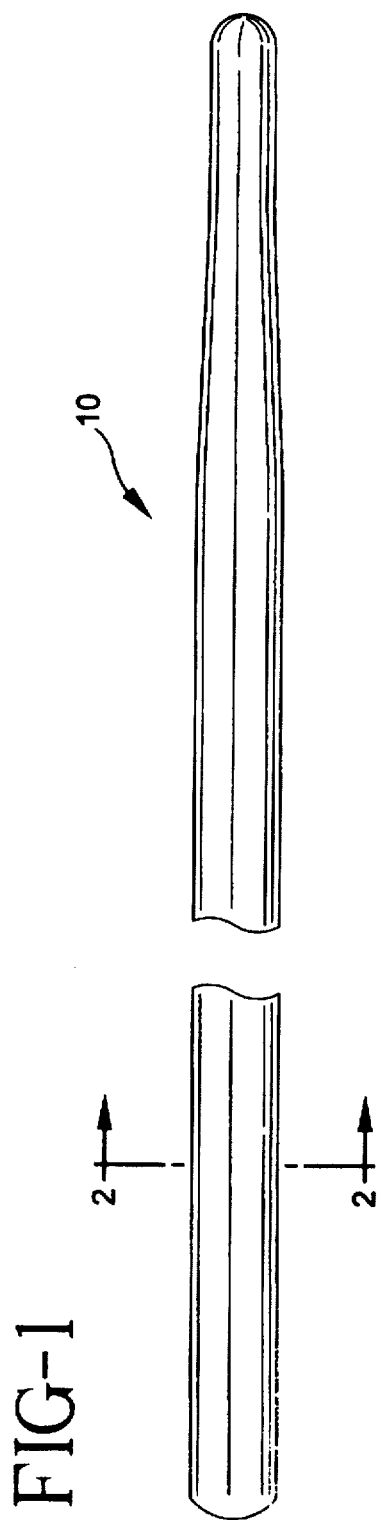
FIG. 1 is a top plan view of a coated guidewire prepared in accordance with the invention.
Figure 2:
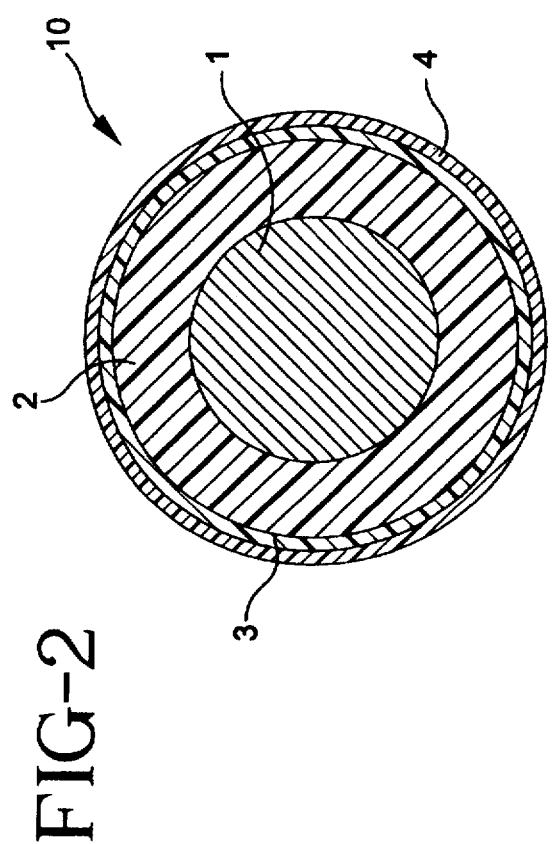
FIG. 2 is an enlarged cross-sectional view taken along line II–II of the guidewire of FIG. 1.

A coated guide wire prepared in accordance with the invention is illustrated in FIGS. 1 and 2 and generally designated as 10. Guide wire 10 includes a metallic core 1 which is tapered at its forward end as to facilitate the manipulation of guide wire 10.

As shown in FIG. 2, metallic core 1 is surrounded by a polymer tube 2 which is heat sealed to the exterior surface of metallic core 1. A first coating 3 formed from an aqueous polymer emulsion, such as an acrylic or polyether block amide latex, is coated on polymer tube 2. First coating 3 is then covered with a second coating 4 of a water soluble hydrophilic polymer.

Surprisingly, it has been found that coatings prepared from a number of aqueous polymer emulsions (latexes) are capable of adhering to both plastic and metal surfaces after curing if the curing is effected after application of the second coating, and that a large number of hydrophilic polymers are capable of adhering to the inner latex layer.

Thus, if the inner coating is cured prior to the application of the second coating the desired adherence is not obtained.

A particularly preferred group of latexes is acrylic latexes, such as latexes based on acrylates, methacrylates, acrylonitrile, acrylamide acrylic acid and methacrylic acid.

The polymer emulsion may contain various additives to accelerate the polymerisation, such as water-soluble resin, e.g. melamin resin, in a concentration of about 5%.

Also other latex types, such as isopren and styrene latexes, may form satisfactorily adhering coatings under certain circumstances. The aqueous emulsion (latex) preferably has a dry matter content of 25–60%.

The first coating composition is conveniently applied by dipping the instrument into the aqueous emulsion and by withdrawing it from the emulsion at a predetermined rate, e.g.0.5 cm/sec., so as to obtain a desired thickness.

The coating formed is subsequently dried. The drying may be effected by air-drying, e.g. at room temperature, or by heating to a temperature of up to the curing temperature of the latex, e.g. up to 100° C., preferably about 40° C. The drying time will normally be from 2 to 20 minutes depending on the drying temperature. At a drying temperature of about 20° C. the drying time is typically 15 minutes.

The second coating composition preferably consists of an aqueous solution of the water-soluble hydrophilic polymer.

Examples of suitable hydrophilic polymers are:

(1) Homopolymers or copolymers of acrylates, methacrylates, acrylonitrile, acrylamide, such as polyacrylamide products commercially available under the trade names "Separan", "Purifloc", "Magnafloc" and "Hercules", acrylic acid, such as polyacrylic acid products commmercially available under the trade names "Carbopol", "Versicol" and "Primal", and methacrylic acid.

(2) Carboxymethyl cellulose.

(3) Copolymers of maleic acid anhydride and vinyl ether, such as a product commercially available under the trade name "Gantrex".

(4) Polysaccharides, such as dextran.

The hydrophilic polymer is preferably present in the aqueous solution in a concentration of from 0.5 to 5 percent by weight and typically of about 1.25 percent by weight.

The application of the second coating is conveniently effected in the same manner as that of the first coating, i.e. by dipping the pre-coated instrument into the aqueous solution and by withdrawing the instrument from the solution at a predetermined rate.

Subsequently, the coating is dried, e.g. at room temperature for a period of from 5 to 20 minutes.

As mentioned above the curing of the inner layer is carried out after the formation of the outer layer. As set forth the curing should be carried out at a temperature of above 100° C., and it is preferably carried out at a temperature of above 130° C., e.g. at a temperature of above 140° C., such as 160°–180° C., for up to 1 hour because the coating obtains the highest wear resistance by treatment at high temperatures.

After curing the instrument is optionally washed with water to remove additives, e.g. surfactants, if any. The wash with water may take from a few minutes and up to 24 hours.

Eventually the instrument is subjected to a final drying, e.g. at room temperature.

Furthermore, the invention relates to a medical instrument having a low-friction coating when wetted, which coating consists of an inner layer of a water-insoluble polymer and an outer layer of a water-soluble hydrophilic polymer, which instrument is characterized in that the inner layer consists of an acrylic polymer.

Surprisingly, it has been found that coatings having an inner layer consisting of an acrylic polymer produce friction values which have friction properties which are at least as good as the friction properties obtained with the known coatings wherein polyurethanes are used as inner layer. This will be evidenced by the method of measuring friction discussed below.

The acrylic polymer is preferably selected from a group consisting of homopolymers and copolymers of acrylates, methacrylates, acrylonitrile, acrylamide, acrylic acid and methacrylic acid.

In a preferred embodiment of the invention the guide wire includes a metallic core, such as a stainless steel core, and a polymer tube placed over the metallic core, the polymer being a polymer selected from the group consisting of polyurethanes and polyester block amides.

The polymer tube is coated on its outer surface with a first coating of an acrylic polymer from an aqueous polymer solution, and subsequently coated with a second aqueous solution of a hydrophilic coating such as a polyacrylamide over the first coating.

The invention will now be described in further detail with reference to the following examples. These examples are presented for purposes of illustration only and not in a limiting sense.

EXAMPLE 1 a) A guide wire consisting of stainless steel having a diameter of 0.2 mm and wound into a coil with close windings having an outer diameter of 0.889 mm was cleaned by dipping into methylene chloride.

Subsequently a first coating consisting of a blend of:

| | |
|---|---|
| Acrylic latex, 50% dry matter content | 230 g |
| Melamin resin, 80% dry matter content | 6.5 g |
| Catalyst solution | 5.0 g |
| Water | 10.0 g. | was applied to the guide wire.

The catalyst solution consisted of 5 g of oxalic acid, 26 g of dimethylamino ethanol and 69 g of water.

The coating was applied by quickly dipping the guide wire into the blend and subsequently withdrawing it from the blend at a rate of 0.5 cm/sec.

The coating thus formed was air-dried at 20° C. for 20 minutes followed by application of a further coating of a hydrocolloid solution consisting of 2.5 g polyacrylamide ("Separan NP10, Dow Chemical Company) dissolved in 97.5 g water. The second coating was applied in the same manner as the first coating.

The coated guide wire was air-dried for 20 minutes and then oven-dried in a hot-air oven at 140° C. for 40 minutes. Finally, it was cooled to ambient temperature.

b) For comparison a similar guide wire was coated with a two-layer hydrophilic coating, the first layer consisting of a polyurethane containing free isocyanate groups and the second layer consisting of a copolymer of maleic acid and vinyl ether ("Gantrez AN179" from GAF) as described in example 11 in EP patent publication No. 0 166 998.

The friction of the coatings formed after wetting with water was measured.

The measurement of the friction was carried out with a measuring apparatus comprising a rotatable disc mounted on a horizontal axis and having a diameter of 100mm and a width of 20 mm. The periphery of the disc was covered with synthetic wash leather which was kept wetted by keeping the disc dipped into a water bath over about 15 mm of the periphery of the disc. The disc was driven by an electric motor at 60 r.p.m.

In measuring the friction one end of the guide wire was secured to a spring dynamometer and the other end was placed around the rotating disc in the direction of rotation and towards a clamp which via a pull string placed across a pulley and loaded with weights could generate a given static pull in the guide wire.

The guide wire was in contact with the wetted wash leather over 180° of the periphery of the disc. The weight load produces a given pull force (pre-stress) which in the following is designated P2, and the friction between guide wires and disc produces an extra force which can be recorded on the dynanometer. In the following this force is designated P1.

The friction of the coating according to the invention was measured at four different pre-stress loads (=P2), viz. 0.2, 0.7, 1.7 and 3.58 Newton, and measurements of friction of the known coating were carried out at three different pre-stress loads, viz. 0.7, 1.7 and 3.58 Newton.

The coefficient of friction can be calculated on the basis of the following formula:

$$\mu = \frac{\ln (P1/P2)}{\pi}$$

The results obtained will appear from tables 1 and 2.

TABLE 1

| Measurement of friction of coating according to the invention | | | | |
|---|---|---|---|---|
| Recorded force (=P1), N | 0.25 | 0.9 | 2.3 | 4.6 |
| Pre-stress load (=P2), N | 0.2 | 0.7 | 1.7 | 3.58 |
| Coefficient of friction, μ | 0.07 | 0.08 | 0.09 | 0.08 |

TABLE 2

| Measurement of friction of known coating | | | |
|---|---|---|---|
| Recorded force (=P1), N | 0.96 | 2.75 | 4.5 |
| Pre-stress load (=P2), N | 0.7 | 1.7 | 3.58 |
| Coefficient of friction, μ | 0.10 | 0.09 | 0.07 |

As will appear from the two tables the coating according to the invention produces a friction which is essentially the same as the friction obtained with the known coating.

EXAMPLE 2

A number of guide wires of stainless steel were coated with separate latex coatings in the manner set forth in example 1.

Two commercially available acrylic latexes were used, viz. "Polysar latex 6779" marketed by Polysar Nederland B.V. and "Acronal LN579S" marketed by BASF AG.

In some cases latexes blended with melamin resin as set forth in example 1 were used, and in other cases they were used as delivered (50% dry matter content) but diluted to a 40% dry matter content.

The coated guide wires were dipped into aqueous solutions of the hydrocolloids set forth in example 3. After air drying the coatings were cured at 130°–140° C. for 30 minutes. Subsequently the guide wires were dipped into water and the coefficient of friction was determined in the manner set forth above. The results obtained will appear from table 3.

TABLE 3

| Coefficient of friction of coatings based on acrylic latexes | | | | | | |
|---|---|---|---|---|---|---|
| | | | | Pre-stress load (= P2), N | | |
| Test No. | Latex | Melamin | Hydrocolloid | 0.2 | 0.7 | 1.7 | 3.58 |
| | | | | Coefficient of friction | | | |
| 1 | Acronal LN579S | | Separan NP20[1] | 0.13 | 0.13 | 0.13 | 0.12 |
| 2 | – | + | – | 0.13 | 0.14 | 0.13 | 0.10 |
| 3 | – | | Separan NP10[2] | 0.07 | 0.08 | 0.07 | 0.08 |
| 4 | – | | – | 0.07 | 0.08 | 0.09 | 0.08 |
| 5 | – | + | – | 0.07 | 0.13 | 0.15 | 0.18 |
| 6 | – | | Versicol S 25[3] | 0.07 | 0.18 | 0.21 | 0.19 |
| 7 | Polysar 6779 | | Veriscol WN23[4] | 0.12 | 0.11 | | |
| 8 | – | | – | | | | |
| 9 | Acronal LN579S | | Versicol W 17[5] | 0.16 | 0.17 | 0.18. | |
| 10 | – | | – | 0.86 | | | |
| 11 | – | | Separan NP10[2] | 0.86 | | | |
| 12 | – | | Carbopol 907[6] | 0.07 | 0.14 | 0.15 | 0.14 |
| 13 | – | | CMC 9H4[7] | 0.18 | 0.14 | 0.14 | 0.12 |
| 14 | – | | Dextran[8] | 0.13 | 0.13 | 0.13 | 0.16 |
| 15 | – | | Versicol F25[9] | 0.18 | 0.16 | | |
| 16 | – | | Magnafloc. 351[10] | 0.13 | 0.26 | 0.26 | |

[1]"Separan NP20" is a non-ionic acrylamide polymer marketed by Dow Chemical Company.
[2]"Separan NP10" is an acrylamide copolymer having a molecular weight of 1–3 · 10$^5$ marketed by Dow Chemical Company.
[3]"Versicol S 25" is a polyacrylic acid having a molecular weight of about 20 · 10$^5$ marketed by Allied Colloids.
[4]"Versicol WN23" is the sodium salt of a polyacrylamide having a molecular weight of 7.5 · 10$^6$ marketed by Allied Colloids.
[5]"Versicol W 17" is a polyacrylamide having a molecular weight of about 500,000 marketed by Allied Colloids.
[6]"Carbopol 907" is a linear polyacrylic acid marketed by Union Carbide.
[7]"CMC 9H4" is carboxymethyl cellulose marketed by Hercules.
[8]"Dextran" is type T 2000 marketed by Pharmacia.
[9]"Versicol F25" is an acrylamide copolymer having a molecular weight of 13 · 10$^6$ marketed by Allied Colloids.
[10]"Magnafloc 351" is a polyacrylamide marketed by Allied Colloids.

As will appear from Table 3, "Separan NP10" produces the lowest coefficient of friction whereas the other hydrocolloids produce coefficients of friction which are slightly higher but fully satisfactory for a number of purposes.

In order to illustrate the adhesion of the coatings a scraping test was performed by means of an apparatus consisting of two catheter tips one tip being secured to a movable and the other being secured to a fixed block of acrylic plastic and in such a manner that the angle between the axes of the catheter tips can be adjusted while at the same time keeping them constantly spaced.

By pulling a wetted guide wire provided with a low-friction coating through the two catheter tips placed at different angles it was possible to determine under a stereomicroscope the angle at which the coatings started being scraped off from the edge of one catheter tip. The greater the angle between the catheter tips is at the beginning of the scraping, the greater the adherence. The maximum obtainable angle was 45°.

A number of coatings according to the invention prepared as set forth in example 2 were compared with a known coating as set forth in example 1.

The test results obtained are set forth in table 4.

TABLE 4

Determination of adherence based on scraping angles

| Test No. | Latex | Melamin | Hydrocolloid | Catheter angle in degrees | | | | |
|---|---|---|---|---|---|---|---|---|
| 17 | Acronal LN579S | | Separan NP20 | 30 | 35 | 35 | 30 | 35 |
| 18 | — | + | — | 35 | 35 | 30 | 35 | 35 |
| 19 | — | | Separan NP10 | 45 | 45 | 45 | 45 | 45 |
| 20 | — | | — | 45 | 45 | 45 | 45 | 45 |
| 21 | — | + | — | 45 | 45 | 45 | 45 | 45 |
| 22 | — | | Versicol S 25 | 25 | 20 | 20 | 20 | 15 |
| 23 | Polysar 6779 | | Versicol WN23 | 20 | 20 | 20 | 25 | 25 |
| 24 | Acronal LN579S | | Versicol W 17 | 20 | 20 | 30 | 30 | 35 |
| 25 | — | | — | 45 | 45 | 45 | 45 | 45 |
| 26 | — | | Carbopol 907 | 20 | 30 | 30 | 40 | 30 |
| 27 | — | | CMC 9H4 | 40 | 40 | 40 | 45 | 40 |
| 28 | — | | Dextran | 35 | 35 | 35 | 40 | 40 |
| 29 | — | | Versicol F25 | 20 | 20 | 20 | 25 | 25 |
| 30 | — | | Magnafloc. 351 | 15 | 10 | 5 | 5 | 10 |
| 31 | Known coating as set forth in example | | | 4 | 6 | 3 | 5 | 3 |

As will appear from the above test results, the adherence of the coatings according to the invention is generally considerably higher than the adherence of the known coating.

EXAMPLE 3

A stainless steel guide wire as described in example 1 was coated with a first layer of a dispersion of an aromatic polyurethane ("Neo Rex R 940" marketed by Polyvinyl Chemie) and having a dry matter content of 35%.

After being dried the guide wire thus coated was coated with a second layer of a 1% aqueous solution of a polyacryl amide ("Versicol WN23") in water in the same manner as described in example 1.

The coated guide wire was dried in air for 30 min. and was subsequently cured at 145° C. for 30 min.

The coated guide wire was then soaked in water for 30 sec. and the friction was evaluated manually by moving fingers over and in contact with the coating. The friction was found to be similar to the friction of the coating of the invention described in example 1.

EXAMPLE 4

A thin polyurethane tube ("Pellethane 2363" marketed by Dow Chemical Company) having an inner diameter of 0.4 mm and an outer diameter of 0.85 mm was introduced onto a guide wire core of stainless steel and having an external diameter of 0.4 mm so as to fully cover the guide wire core. The core and tube were then heated to about 185° C. for 5 min. to heat seal the tube to the metallic core.

A first coating composition consisting of a mixture of:

| | |
|---|---|
| Acrylic latex ("Acronal LN 5795"), 50% dry matter | 400 g |
| Water | 100 g | was applied to the guide wire by quickly dipping it in the coating composition and subsequently withdrawing it therefrom at a rate of 0.5 cm/sec.

The first coating thus formed was air dried for 30 min. at 20° C. and then a second coating composition consisting of:

| | |
|---|---|
| Polyacryl amide ("Versicol WN 23") | 10 g |
| Water | 1000 ml | was applied on top of the first coating in the same manner as the first coating composition.

The guide wire thus coated was air dried for 30 min. and was then cured at 160° C. for 1 hour before it was cooled to ambient temperature.

Following wetting with water the friction of the coating was measured as described in example 1.

The results obtained will appear from table 5.

TABLE 5

Measurement of friction of coating according to the invention.

| | |
|---|---|
| Recorded force (=P1), N | 0.9 |
| Pre-stress load (=P2), N | 0.7 |
| Coefficient of friction μ | 0.08 |

The adherence of the coating was determined by the scraping test described above. The test results obtained will appear from table 6.

TABLE 6

Determination of adherence based on scraping angles.

| Test No. | Latex | Hydrocolloid | Catheter angle in degrees |
|---|---|---|---|
| Example 4 | Acrylic | Polyacryl amide | 30, 30, 35, 35, 35 |

EXAMPLE 5

A guide wire similar to that of example 4 except that the thin tube was made from a polyether block amide ("Pebax" marketed by Atochem) was prepared and tested. The data obtained by measuring the friction of the wetted coating were similar to the data set forth in table 5.

EXAMPLE 6

A series of microscope slides made from glass were dipped into a latex of the same composition as the first latex coating composition described in example 4. After drying the coated slides were dipped into a solution of the same composition as the second polyacryl amide coating composition described in example 4.

The coating thus formed was dried for 30 min. at room temperature and was subsequently cured in an oven for 30 min. at a temperature of 160° C. The coated slides were weighed and were washed by applying sterile water to the coating and by moving a finger over the coating for about 2 min. on each side.

The friction coefficient was found to be essentially the same as the friction coefficient of the coating described in example 4.

The slides were finally dried and weighed again. The washing of the slides resulted in a weight loss of only 0.0001 g (from 4.6208 g) which shows that the adherence of the hydrophilic coating to the glass surface is excellent.

We claim:

1. A method of reducing the surface friction of a medical instrument with a hydrophilic, low-friction coating comprising:

applying a first coating of an aqueous emulsion of a water-insoluble latex to said medical instrument;

drying said first coating without curing said water-insoluble latex;

applying a second coating of an aqueous solution of a water-soluble hydrophilic polymer to said first coating and drying said second coating; and curing said first coating and said second coating simultaneously by heating to a temperature greater than about 100° C.

2. A method according to claim 1, wherein said first coating is an aqueous emulsion of an acrylic latex selected from the group consisting of latexes based on acrylates, methacrylates, acrylonitrile, acrylamide, acrylic acid, methacrylic acid and mixtures thereof.

3. A method according to claim 1, wherein said first coating is an aqueous emulsion of a latex selected from the group consisting of isoprene and styrene.

4. A method according to claim 1 further comprising adding a polymerization acceleration additive to said first coating.

5. A method according to claim 4, wherein said additive is a water-soluble resin.

6. A method according to claim 5, wherein said water-soluble resin is a melamin resin.

7. A method according to claim 5, wherein said second coating includes an aqueous solution selected from the group consisting of solutions of a carboxymethyl cellulose, a copolymer of maleic acid anhydride, a vinyl ether, and a polysaccharide.

8. A method according to claim 7, wherein said polysaccharide is dextran.

9. A method according to claim 1, wherein said second coating includes an aqueous solution selected from the group consisting of solutions of a homopolymer or copolymer of a material selected from the group consisting of acrylate, methacrylate, acrylonitrile, acrylamide, acrylic acid or methacrylic acid.

10. A method according to claim 1, wherein said curing is accomplished by heating to a temperature of above about 130° C.

11. A method according to claim 1, wherein said medical instrument is a guide wire.

12. A method according to claim 11, wherein said guide wire is metallic.

13. A method according to claim 1, wherein said medical instrument includes an instrument core.

14. A method according to claim 13, further comprising providing a polymer tube over said instrument core prior to applying said aqueous emulsion coating.

15. A method according to claim 13, wherein said polymer tube includes a polymer selected from the group consisting of polyurethane and polyester block amides.

* * * * *